United States Patent [19]

Saito et al.

[11] Patent Number: 4,830,502
[45] Date of Patent: May 16, 1989

[54] APPARATUS AND METHOD FOR MEASURING LIGHT ABSORPTION CHARACTERISTIC OF A THIN FILM, AND EQUIPMENT PROVIDED WITH SAID APPARATUS FOR FORMING A MONOMOLECULAR BUILT-UP FILM

[75] Inventors: Kenji Saito, Tokyo; Yukuo Nishimura, Sagamihara; Yoshinori Tomida, Yokohama; Haruki Kawada, Kawasaki; Ken Eguchi, Yokohama; Takashi Nakagiri, Tokyo, all of Japan

[73] Assignee: Canon Kabushiki Kaisha, Tokyo, Japan

[21] Appl. No.: 799,497

[22] Filed: Nov. 19, 1985

[30] Foreign Application Priority Data

| Nov. 20, 1984 | [JP] | Japan | 59-243183 |
| Nov. 20, 1984 | [JP] | Japan | 59-243184 |
| Nov. 20, 1984 | [JP] | Japan | 59-243185 |
| Nov. 20, 1984 | [JP] | Japan | 59-243186 |
| Nov. 20, 1984 | [JP] | Japan | 59-243187 |
| Nov. 20, 1984 | [JP] | Japan | 59-243188 |
| Nov. 20, 1984 | [JP] | Japan | 59-243189 |
| Nov. 20, 1984 | [JP] | Japan | 59-243190 |
| Jul. 8, 1985 | [JP] | Japan | 60-148320 |

[51] Int. Cl.$^4$ ........................................... G01N 21/00
[52] U.S. Cl. ..................................... 356/432; 356/440
[58] Field of Search ............ 356/436, 440, 434, 432 T, 356/434 O, 436 D, 436 A, 440 T, 440 A

[56] References Cited

U.S. PATENT DOCUMENTS

| 4,468,136 | 8/1984 | Murphy et al. | 336/432 T |
| 4,529,319 | 7/1985 | Müller | 356/432 T |

OTHER PUBLICATIONS

"Trace Analysis In Gases Laser Induced Schlieren Technique", Hermann et al., *Infrared Physics*, vol. 19, #3, pp. 455-459, 8/1979.
"Photothermal Deflection Spectroscopy and Detection", Jackson et al., *Applied Optics*, vol. 20 #8, pp. 1333-1344, Apr. 1981.
"Second Sound Spectroscopy: A New Method for Studying Optical Absorption In Solids", Smith et al., *Physics Letters*, vol. 56A, #3, pp. 223-224, 3/1926.
"Internal-Reflection Spectroscopy", Molm et al., *Laser Focus*, Aug. 1979, pp. 60-65.

*Primary Examiner*—Richard A. Rosenberger
*Attorney, Agent, or Firm*—Fitzpatrick, Cella, Harper & Scinto

[57] ABSTRACT

An apparatus for measuring a light absorpiton characteristic of a thin film is provided.

The apparatus comprises (1) a liquid container containing a liquid on which surface a thin film is to be spread, (2) exciting light source for supplying an exciting light to be projected from below the liquid surface on to a measurement site of the thin film spread on the liquid surface, at such an incident angle that the exciting light reflects totally at the liquid surface, (3) a chopper for converting the exciting light into an intermittent exciting light before the exciting light reaches the measurement site of the thin film, (4) a probe light source for supplying probe light passing the measurement site or its vicinity, and (5) a detector for detecting an amount of deflection of the probe light having passed the measurement site or its vicinity. A method for measuring the light absorption characteristic of a thin film and an equipment for forming a monomolecular built-up film employing the above apparatus are also provided.

11 Claims, 6 Drawing Sheets

APPARATUS AND METHOD FOR MEASURING LIGHT ABSORPTION CHARACTERISTIC OF A THIN FILM, AND EQUIPMENT PROVIDED WITH SAID APPARATUS FOR FORMING A MONOMOLECULAR BUILT-UP FILM

BACKGROUND OF THE INVENTION

1. Field of the Invention

This invention relates to an apparatus and a method for optically measuring the characteristics of a thin film particularly spread on a liquid surface, as well as to equipment provided with said apparatus, for forming a monomolecular built-up film. More particularly, the present invention relates to an apparatus and a method for measuring the light absorption characteristic of a thin film which provides a basic data for analysis of the characteristics of said thin film. The present invention is utilized in, for example, analysis of the characteristic of a monomolecular film spread on a liquid surface to be formed into a monomolecular built-up film.

2. Description of the Prior Art

Conventional apparatuses have been developed for measuring the light absorption characteristic of a sample, and for measuring said characteristic form the transmissivity or reflectivity of the sample. However, when a light is applied to a sample, there appears a scattered light in addition to a transmitted light and a reflected light. In order to conduct an evaluation of the light absorption characteristic of a sample with high precision, it is important to directly measure a light component absorbed by the sample.

Apparatuses for directly measuring the absorbed light component include photoacoustic spectroscopy (PAS) apparatus and a photothermal radiometry (PTR) apparatus utilizing a phenomenon that, when a light is intermittently applied to a sample, the light energy absorbed by the sample is intermittently converted to heat by a radiationless relaxation process.

The PAS apparatus is classified into a microphone type and a piezoelectric element type. In the microphone type a sample needs to be placed in a closed chamber, and in the piezoelectric element type, the arrangement of a detector and a sample is important. Any of these types are not suitable for the measurement of a thin film spread on a liquid surface. In the PTR apparatus which uses an infrared detector, the measurement is easily affected by the atmospheric conditions such as humidify or the like.

Another apparatus for directly measuring a light component that is absorbed is a photothermal deflection spectrosocpy (PDS) apparatus. This apparatus utilizes the phenomenon that the sample which has absorbed a light generates heat, which causes a temperature distribution within the sample and in its vicinity, and that this temperature distribution changes the refractive indexes of the sample and its vicinity and therefore the light coming into the sample is deflected.

In other words, in PDS apparatus, two kinds of light are projected onto the measurement site; one kind is exciting light which generates heat in the sample upon light absorption to cause the temperature distribution to change the refractive index and the other is probe light for detecting deflection of the exciting light caused by the above- mentioned change of the refractive index, and therefore the light absorption characteristic of the sample is measured from the length of the exciting light and the deflection of the probe light. The PDS apparatus is suitable for field measurement or remote measurement because a sample and a detection system can be arranged independently. The apparatus of the present invention is the same as the PDS apparatus in basic principle.

The PDS apparatus are classified into two types, a transverse type and a collinear type according to the arrangement of an exciting light and a probe light. Both types measure the amount of delfection of probe light corresponding to the amount of exciting light absorbed by a sample. The detector is often a position sensitive detector (PSD).

FIG. 10A illustrates an example of the PDS apparatus of the collinear type. An exciting light 11 emitted by an exciting light source 10 is converted into intermittent exciting light by a chopper 12 and is converged by a lens 34 and is projected to a sample 4'. Probe light 6 emitted from a probe light source 5 is allowed to pass the very site of the sample 4' to which the exciting light 11 is projected by means of a lens 35 and a light path regulator 17 such as a mirror or the like and then reaches a detector 7. For this probe light 6, the amount of deflection as shown in a dotted line is measured. FIG. 10B is an example of the PDS apparatus of transverse type. The only difference between this transverse type and the collinear type is that the probe light 6 is applied parallel to the surface of the sample 4'.

The theoretical treatment of the phenomena in the PDS apparatus can be made by solving the equation of heat conduction taking place in a sample. The amount of deflection as measured in terms of deflection angle is proportional to the intensity of exciting light, the temperature coefficient $(\partial n/\partial T)$ of the refractive index, the temperature gradient $(\partial T/\partial K)$ at the portion through which a probe light passes, etc. Terms proportional to the light absorption coefficient of the sample are contained in $(\partial T/\partial K)$. $(\partial n/\partial T)$ can take a positive or negative value depending upon the sample, which implies that the deflection angle, can be positive or negative.

The PDS apparatus, when applied to a measurement for a thin film spread on a liquid surface, has the following disadvantages because the film as a sample is extremely thin. "A thin film spread on a liquid surface" in this specification means a thin film extended over a liquid surface without sinking or floating, such as a monomolecular film.

In a thin film spread on a liquid surface, the path through which exciting light travels is short and consequently the exciting light is liable to be affected by external environments before the exciting reaches the liquid surface, such as dusts and fluctuation in the air, and so on. Moreover, the S/N ratio is reduced also by reflected light or transmitted light after the exciting light has reached the thin film. Thus, measurement with good precision and good sensitivity is hardly obtainable. In some cases, measurement is conducted in such a way that there is used, as a gas phase present over a liquid surface, a special gas which interacts with a thin film on the liquid surface. In such a measurement, it is necessary to make a portion of the gas through which the exciting light passes as short as possible; however, realization of such a measurement is difficult.

SUMMARY OF THE INVENTION

An object of the present invention is to achieve a good precision and good sensitivity measurement of the light absorption charactertistic of a special sample which is very thin, namely, a thin film spread on a liquid surface.

The above object can be achieved by the present invention which is described below.

According to an aspect of the present invention, there is provided an apparatus for measuring the light absorption characteristic of a thin film, which comprises:

a liquid container containing a liquid on which surface a thin film is to be spread, an exciting light source for supplying an exciting light to be projected from below the liquid surface to a measurement site of the film spread on the liquid surface, at such an incident angle that the exciting light reflects totally on the liquid surface, a chopper for converting the exciting light into an intermittent exciting light before the exicting light reaches the measurement site of the thin film, a probe light source for supplying probe light passing the measurement site or its vicinity, and a detector for detecting the amount of deflection of the probe light having passed the measurement site or its vicinity.

According to another aspect of the present invention, there is provided an apparatus for measuring the light absorption characteristic of a thin film, which comprises:

a liquid container containing a liquid on which surface a thin film is to be spread where at least a part of the liquid surface is left without being covered by the thin film, an exciting light source for supplying an exciting light, a light path splitting means for splitting the exciting light supplied into (a) an exciting light portion to be projected from below the liquid surface on to a measurement site of the thin film spread on the liquid surface, at such an incident angle that the exciting light portion (a) reflects totally on the liquid surface and (b) an exciting light portion to be applied from below the liquid surface to a reference site of the uncovered liquid surface part, at such an incident angle that the exciting light portion (b) applied reflects totally on the liquid surface.

a chopper for converting the exciting light into intermittent exciting light before the exciting light reaches the measurement site and the reference site, a probe light source for supplying probe light, a light path splitting means for splitting the probe light supplied into (a) a probe light portion passing the measurement site or its vicinity and (b) a probe light portion passing the reference site or its vicinity, and a detector for detecting the amounts of deflection of the probe light portion (a) having passed the measurement site or its vicinity and the probe light portion (b) having passed the reference site or its vicinity.

According to a further aspect of the present invention, there is provided a method for measuring the light absorption characteristic of a thin film wherein an exciting light is intermittently projected to a measurement site of a thin film spread on a liquid surface, and simultaneously a probe light is projected to the measurement site or its vicinity, and the light absorption characteristics of the thin film are measured from the amount of deflection of the probe light, the exciting light being projected to the measurement site if the light from the liquid side is at such an incident angle that the exciting light applied reflects totally at the liquid surface.

According to a still further aspect of the present invention, there is provided equipment for forming a monomolecular built-up film which comprises an apparatus for measuring the light absorption characteristic of a monomolecular film, the apparatus comprising:

an exciting light source for supplying an exciting light to be projected to a measurement site of a monomolecular film spread on a liquid surface from below the liquid surface at such an incident angle that the exciting light reflects totally on the liquid surface, a chopper for converting the exciting light into an intermittent exciting light before the exciting light reaches the measurement site, a probe light source for supplying a probe light passing the measurement site or its vicinity, and a detector for detecting the amount of deflection of the probe light having passed the measurement site or its vicinity.

DETAILED DESCRIPTION OF THE PREFERRED EMBODIMENTS

The refractive index of a thin film sample will change at an exciting-light-irradiated site and its vicinity when the sample absorbs the exiting light. Accordingly the light absorption characteristics can be measured by utilizing the above phenomenon as a function of deflection of the probe light beam. The principle itself is the same as that of the conventional PDS apparatuses.

In the present invention, the object of measurement is a thin film spread on a liquid surface, and an exciting light beam is projected onto this thin film from the liquid side so that the light can reflect totally at the liquid surface on which the thin film spreads. Unlike a case in which a light beam is projected through the air, the exciting light is not affected by dust and fluctuations in the air. Further, the measurement is not affected by transmitted light passing through the thin film into the air over the thin film, since the exciting light projected onto the thin film reflects totally at the liquid surface and the transmitted light in a form of a very slight evanescent wave has a short wavelength. Furthermore, no adverse effect is caused by irregular reflection because the exciting light reflects regularly at the liquid surface.

The present invention will be described below in detail by referring to the accompanying drawings.

Figure 1:
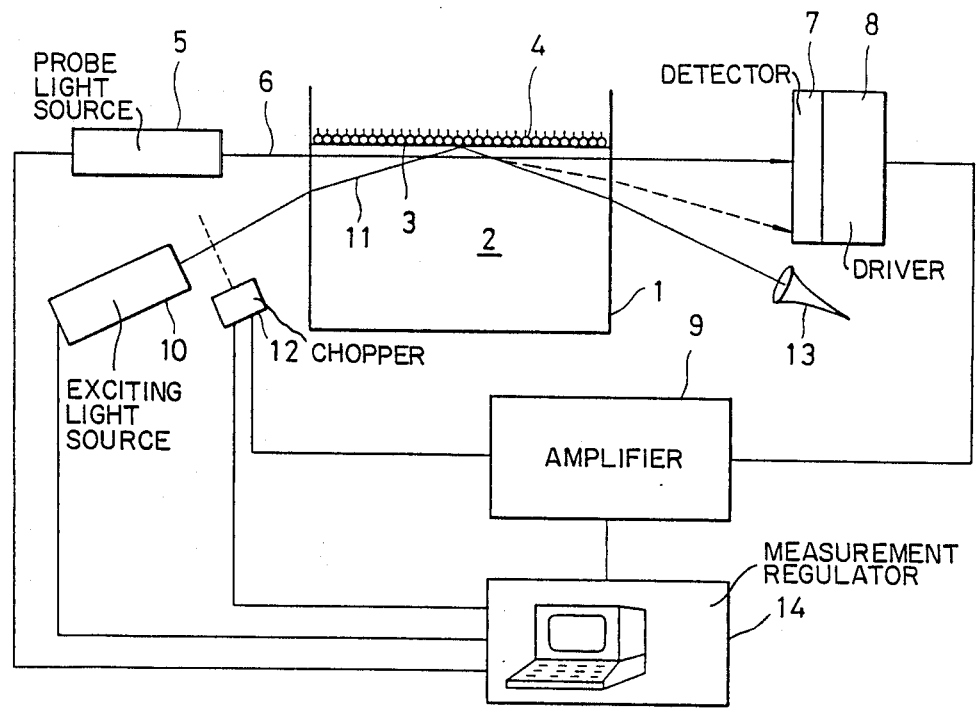
FIG. 1 is a drawing showing one embodiment of the present invention.

In FIG. 1, 1 refers to a liquid container containing a liquid 2. On the liquid surface 3 is spread a thin film 4 as a sample. The thin film 4 represents a schematic illustration of a monomolecular film.

A probe light source 5 is provided at one side of the liquid container 1. This probe light source 5 supplies a probe light 6 which proceeds parallel to the liquid surface 3 just below the liquid surface 3. A detector 7 for detecting the position of the probe light transmitted is provided at other side of the liquid container 1 so that the probe light source 5 and the detector 7 oppose each other via the liquid container 1. The detector 7 sends detector signals to a lock-in amplifier 9 through a driver 8.

An exciting light source 10 is provided slightly below the probe light source 5. This exciting light source 10 supplies exciting light 11 which is projected to a measurement site of the thin film from the side of the liquid 2 at such an angle that the exciting light 11 reflects totally at the liquid surface 3 on which the thin film spreads. At one position on the path of the exciting light 11, there is provided a chopper for converting the exciting light 11 into an intermittent exciting light. At one position of the path of the exciting light 11 after on the other side of the liquid container 1, there is provided an absorber 13 for the exciting light 11.

The chopper 12 is connected to the lock-in amplifier 9. By using intermittent signals sent from the chopper 12 as a reference signal, the lock-in amplifier 9 can synchronously detect signals sent from the detector 7. The probe light source 5, the exciting light source 10, the chopper 12 and the lock-in amplifier 9 are connected to a measurement regulator 14. The measurement regulator 14 controls the paths and wavelengths of the probe light 6 and the exciting light 11 as well as the interval of intermission of the exciting light 11 produced by the chopper 12 and further calculates the light absorption characteristic of the thin film sample by using signals sent from the lock-in amplifier 9.

The liquid container 1 need not be transparent as a whole if it has transparent windows at least at the wall portions through which the probe light 6 and the exciting light 11 pass. The liquid 2, as long as its absorption of the exciting light 11 is low, affects little the measurement even if the liquid 2 gives a slight effect directly to the probe light 6. However, the liquid 2 is preferred to be transparent.

The exciting light 11 supplied from the exciting light source 10 is modulated to become an intermittent exciting light beam by the chopper 12 and is projected from below the liquid surface 3 to a measurement site of the thin film 4 spread on the liquid surface 3 in the liquid container 1. The exciting light 11 is projected so that the incident angle is larger than the critical angle of the liquid 2. The exciting light 11 reflects totally at the liquid surface 3, passes through the liquid 2, and leaves the liquid container 1. An evanescent wave appearing as a result of the total reflection diffuses out to a gas phase over the liquid surface 3 but the evanescent wave has shorter wavelength and is very slight in quantity. The exciting light 11 which has left the liquid container 1 is absorbed by the absorber 13, whereby unnecessary light is removed. At the measurement site of the thin film 4 at which the intermittent exciting light 11 reflects totally as well as its vicinity, there occurs light absorption by the thin film 4 and heat is intermittently generated in accordance with a radiationless relaxation process. This causes intermittent variation in the refractive indexes of the measurement site and its vicinity.

The probe light 6 supplied from the probe light source 5 proceeds parallel to the liquid surface 3 just below the liquid surface 3 and accordingly passes through the vicinity of the measurement site where the intermittent change of refractive index occurs due to the irradiation by the exciting light 11. When the probe light 6 passes through this portion of the liquid which experiences an intermittent change of the refractive index, the path of the probe light 6 is deflected, as shown in a dotted line, in accordance with the change of refractive index.

The detector 7 receives the beam of the probe light 6 intermittently and sends a signal relating to the receiving position of the probe light 6 to the lock-in amplifier 9 via the driver 8. The lock-in amplifier 9 receives signals not only from the detector 7 but also from the chopper 12 and by synchronizing these two signals, send to the measurement regulator 14 with a good S/N ratio (a) signals of the position of the probe light 6 received when the exciting light 11 has been irradiated and (b) signals of the position of the probe light 6 received when the exciting light 11 has not been irradiated. Based on the signals sent, the measurement regulator 14 calculates the amount of deflection amount of the probe light 6 relative to the wavelength of the exciting light 11 used and further calculates therefrom the light absorption characteristic of the thin film 4. By conducting similar measurements when gradually altering the wavelength of the exciting light 11, there can be obtained the spectral absorption characteristic of the thin film 4.

In the measurement site can be selected arbitrarily by controlling the path of the exciting light 11 by means of the measurement regulator 14. The path of the probe light 6 can be precisely controlled in accordance with the level of the liquid surface 3 also by means of the measurement regulator 14. Further, all controls necessary for the probe light source 5, the exciting light source 10 and the chopper 12 can be automatically carried out by means of the measurement regulator 14 to simplify the measurement operations.

The light energy absorbed by the thin film 4 can be obtained from the distribution of the amount of the exciting light 11 at the measurement site, the characteristic of thermal change of the refractive index of the liquid 2, the incident position of the probe light 6 and the amount of deflection of the probe light 6. Therefore, by monitoring the energy of the exciting light 11 applied to the thin film 4 by means of a photosensor or the like, the absolute light absorption characteristic of the thin film 4 can be obtained from the light energy absorbed by the thin film 4 and the energy of the exciting light 11 applied to the thin film 4. By altering the wavelength of the exciting light 11, the absolute spectral absorption characteristic of the thin film 4 can be obtained. Further, by measuring the relative strength of the exciting light, depending on its wavelength as well as the amount of deflection of the probe light 6 corresponding to the wavelength of the exciting light 11, the relative spectral absorption characteristic of the thin film 4 can be obtained. The relative or absolute light absorption characteristic can be selected depending upon the purpose of measurement.

Figure 2:
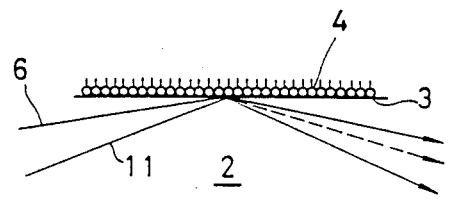
FIGS. 2 to 6 each are a drawing showing other embodiments of the present invention.

The probe light 6, as shown in FIG. 2, may be allowed to reflect totally at the measurement site together with the exciting light 11. In such a case, the probe light 6 can pass through the portion of the liquid 2 having a large change of refractive index, which provides advantages of easier detection of amount of deflection as well as of more precise and more sensitive measurement.

Figure 3:
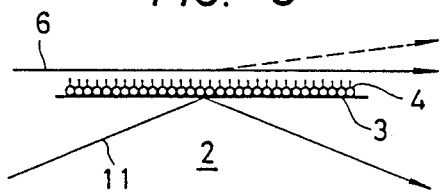

The probe light 6, as shown in FIG. 3, may also be allowed to pass through a gas phase above, but adjacent the liquid surface 3 and thereby to be under the influence of the change of refractive index of the gas phase. Thus the probe light 6 does not intersect the exciting light 11 and consequently the measurement does not undergo any effect due to such an intersection.

Figure 4:
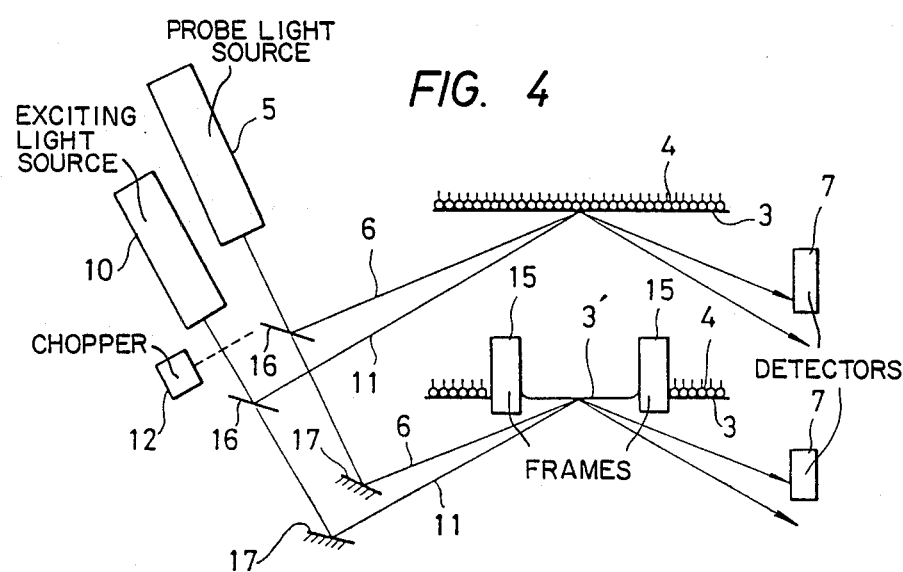

As shown in FIG. 4, the measurement can also be made in such a way that the liquid surface 3 on which the thin film 4 spreads is separated by a partition frame 15 to form a liquid surface 3' having no thin film 4 thereon and this liquid surface 3' is used as a reference liquid surface in the measurement. That is, the probe light 6, supplied from the probe light source 5 and the exciting light 11 supplied from the exciting light source 10 through the chopper, are split by light path splitting means 16, such as beam splitters, half mirrors or the like, and then sent simultaneously to the liquid surfaces 3 and 3'. The deflection amounts of the probe light 6 corresponding to the liquid surfaces 3 and 3' are detected by respective detectors 7. From the difference between these two deflection amounts is obtained the light absorption characteristic of the thin film 4. By using this difference, various effects adversely affecting the measurement can be removed and high precision measurement becomes possible.

Figure 5:
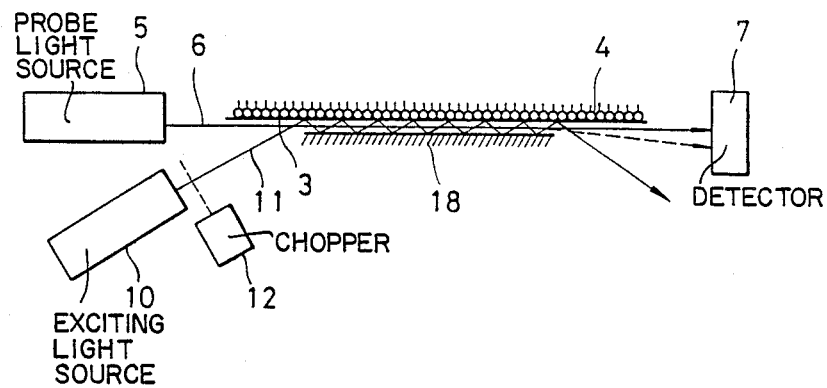

As shown in FIG. 5, the measurement can also be made by allowing the exciting light 11 to cause a multiple reflection. The exciting light 11, supplied from the exciting light source 10, is converted to an intermittent exciting light by the chopper 12, is allowed to reflect totally on the liquid surface 3, is reflected by a mirror surface 18, arranged under the liquid surface 3, and is again applied to the liquid surface 3. By providing the mirror surface 18 parallel to the liquid surface 3, reflection is repeated within the region of the mirror surface 18; thus a plurality of sites of the thin film 4 on the liquid surface 3 are irradiated so that the region in which the change of refractive index takes place is enlarged. When the probe light 6 from the probe light source 5 is allowed to pass through this region, the probe light 6 is deflected at a large angle because the region where the probe light 6 causes deflection is enlarged. By allowing the detector 7 to detect the position deviation of the probe light 6 due to the above reflection, detection can be conducted with high sensitivity. When the incident angle, the distance between the mirror surface 18 and the liquid surface 3 and the length of the reflection region are denoted as $\theta$, d and l, respectively, the number of times N, of the exciting light 6 is reflected, can be represented by the following formula:

$$N = l/(2d \tan \theta)$$

When, for example, l=30 mm, d=0.5 mm and $\theta$=60° C., N is approximately 18 and accordingly the sensitivity of measurement is increased by about 18 times.

Figure 6:
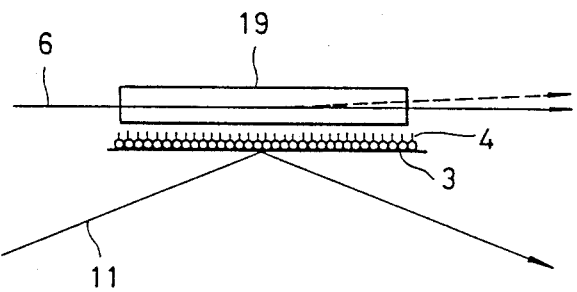

As shown in FIG. 6, the probe light 6 can also be allowed to pass through a medium 19 giving a large change of refractive index, such as a lithium niobate crystal, a titanium oxide crystal, a silicon dioxide crystal, a glass, a plastic or the like, which is provided over but close to the liquid surface 3. The heat generated in the thin film 4 by its light absorption is allowed to act on the medium 19 giving a large change of refractive index which is arranged parallel to the liquid surface 3 and over but close to the thin film 4, whereby said heat is converted to the change of refractive index of the medium 19; the probe light 6 is allowed to pass through this medium 19, whereby the amount of the deflection of the probe light is enlarged; thus, high sensitivity detection is possible.

Figure 7:
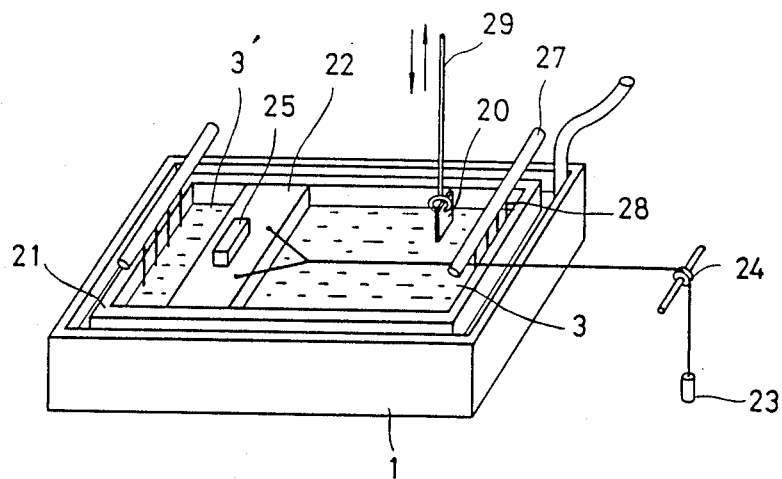
FIGS. 7 and 8 are drawings showing a liquid container and a procedure used in the present invention for the formation of a monomolecular built-up film.
Figure 8:
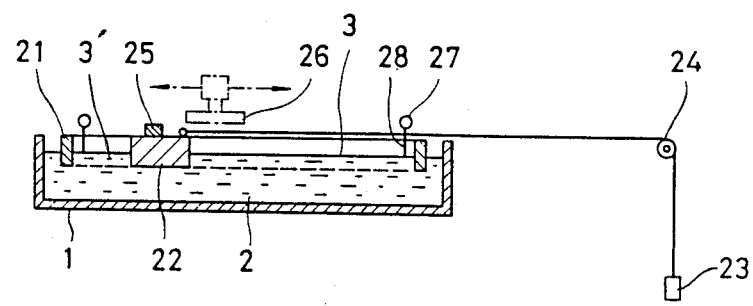

In the measurement of light absorption characteristic according to the present invention it is advantageous to use a liquid container 1 as shown in FIGS. 7 and 8 which can be effectively utilized for the formation of a monomolecular built-up film.

When a monomolecular built-up film is prepared in accordance with a monomolecular film building-up method called the Langmuir-Blodgett's method after the inventor of the method (hereinafter, referred to as the LB method; reference is made to Shin Jikken Kagaku Koza, Vo., 18, 498 to 507 pages, Maruzen), a monomolecular film formed on a liquid surface 3 is transferred onto the surface of a substrate 20 and such a monomolecular film is built-up one by one to prepare an ultra-thin film. Accordingly, the characteristic of the monomolecular film formed on the liquid surface 3 is important. The structure and molecular orientation in the monomolecular built-up film transferred onto the substrate 20 according to the LB method are naturally based on the condition of the monomolecular film spread on the liquid surface 3. However, there is a problem as to whether the film keeps it state when transferred onto the substrate 20. The present invention can be utilized to examine whether or not the state of the monomolecular film spread on the liquid surface 3 has been exactly transferred onto the substrate 20. A liquid container 1 for forming a monomolecular built-up film as well as a procedure therefor will be described below.

As shown in FIGS. 7 and 8, inside a shallow and square large liquid container 1 containing a liquid 2 is horizontally suspended an interior frame 21 made of, for example, a polypropylene material or the like, whereby the liquid surface is divided into portion 3 and portion 3'. Pure water is usually employed as the liquid 2. Inside the interior frame 21 is floated a film formation frame 22 made also of, example, a polypropylene or the like. The film formation frame 22 is a rectangular parallel-epided having a width slightly less than the inside width of the interior frame 21 and can make a two dimensional reciprocating movement (in the left and right directions in FIGS. 7 and 8). To the film formation frame 22 is connected, via a pulley 24, a weight 23 for pulling the film formation frame 22 to the right direction in FIGS. 7 and 8. A magnet 25 is fixed on the film formation frame 22. Above the film formation frame 22 is provided a counter magnet 26 which can move in the left and right directions in FIG. 8 and, when approaching the magnet 25, repulses the magnet 25. Thus, the film formation frame 22 can move in the left and right directions in FIGS. 7 and 8 and also can stop. The film formation frame 22 may be moved directly by using a motor and a pulley in place of the weight 23 and a pair of the magnets 25 and 26.

Inside the interior frame 21 are arranged suction nozzles connected to a suction pump (not shown in FIGS. 7 and 8) via a suction pipe 27. These suction nozzles are used for rapid removal of undesirable substances such as the monomolecular film of the prior step and the like. This prevents by impurities of a monomolecular film or monomolecular built-up film to be prepared. Reference numeral, 20 represents substrate fixed to a substrate holder 29 which is moved vertically.

The process of forming a monomolecular film will now be explained. First, the film formatiom frame 22 is moved; unnecessary substances on the liquid surfaces 3 and 3' such as the monomolecular film of the prior step and the like are swept, pushed and sucked by the suction nozzles 28, thereby cleaning the liquid surfaces 3 and 3'. Then the film formation frame 22 is moved to the left end of the liquid surfaces 3 and 3' and onto the liquid surface are added a few drops of a solution of a film-constituting substance dissolved in a volatile solvent such as benzene, chloroform or the like in a concentration of, for example, up to $5 \times 10^{-3}$ mol/l, by. This solution spreads on the liquid surface 3 and the solvent vaporizes, thereby leaving a monomolecular film on the liquid surface 3.

This monomolecular film exhibits a two-dimensional behavior on the liquid surface 3. When the molecules of the monomolecular film have a low surface density, the film is called a two-dimensional gas film and, between the area occupied by each molecule and the surface pressure, the state equation of two-dimensional ideal gas holds.

Next the film formation frame 22 is moved in the right direction and the area of the liquid surface 3 is decreased, whereby the surface density of the two-dimensional gas film is increased and the interaction between molecules is intensified and the two-dimensional gas film is converted to a two-dimensional liquid film and then into a two-dimensional solid film as the frame continues to decrease the area of surface 3. This solid film is a uniform, ultra-thin film having uniform molecular arrangement and high regularity. Only at this stage can the monomolecular film be successfully transferred onto the substrate 20. By repeating this transfer of the solid monomolecular film a plurality of times, a monomolecular built-up film can be obtained. As the substrate 20, there are used, for example, a glass, a synthetic resin, a ceramic and a metal.

The transfer of the monomolecular film from the liquid surface 3 onto the substrate 20 is conducted mainly by two methods. One is a vertical immersion method and the other is a horizontal lifting method. In the vertical immersion method, while a certain surface pressure suitable for monomolecular film building-up operation is applied to the monomolecular film spread on the liquid surface 3, the substrate 20 is reciprocated in a direction crossing the film, namely, a vertical direction, whereby the monomolecular film is transferred to substrate 20. In the horizontal adhesion method, while the substrate 20 is kept horizontal, the substrate 20 is allowed to approach from above to the liquid surface 3 as close as possible, is tilted slightly and is allowed to touch the monomolecular film at one end, whereby adhesion is carried out.

In order to conduct the transfer onto the substrate 20 under a condition suitable for a monomolecular film, the surface pressure of the monomolecular film is measured. The surface pressure suitable for transfer is considered to be generally 15 to 30 dyn/cm. Outside this range, there tend to occur a disturbance of molecular arrangement and orientation or peeling of film. The above range is regarded as being approximate since a suitable surface pressure may be out of the above range in some cases depending upon, conditions such as the chemical structure of film-constituting substance and temperature.

The surface pressure of the monomolecular film can be measured automatically and continuously using a surface pressure tester (not shown in the drawings). As the surface pressure tester, there are various testers such as a tester measuring a surface pressure indirectly from a difference between surface tensions of the liquid surface 3' uncovered by the monomolecular film and the liquid surface 3 covered by the monomolecular film and a tester directly measuring a two-dimensional pressure applied to the film formation frame 22 floating on the liquid surface 3' uncovered by the monomolecular film and the liquid surface 3 covered by the monomolecular film. Each tester has its own characteristic. Together with the surface pressure of the monomolecular film, there are usually measured the area occupied by each molecule of the monomolecular film and the change of in the area occupied by the film are also usually measured. The occupation area and its change are obtained from the movement of the film formation frame 22 in the left and right directions.

The movement of the film formation frame 22 toward the right for converting the two-dimensional gas film into a two-dimensional solid film is controlled by the surface pressure of the monomolecular film, which is measured by the surface pressure tester. In other words, the surface pressure of the monomolecular film is invariably kept at a constant value selected to be within the range of pressures suitable for the transfer of the film by a driving device (not shown in the drawings) which drives the counter magnet 26 toward the right or left depending on the surface pressure of the monomolecular film measured by a surface pressure tester. This control of the movement of the film formation frame 22 is conducted not only for the time from dropping of the solution of film-constituting substance to start of monomolecular film transfer but also during transfer. In transfer operation, as the transfer of the monomolecular film onto the substrate 20 proceeds, the surface density of this film spread on the liquid surface 3 is reduced and its surface pressure is reduced as well. Accordingly, it becomes necessary to move the film formation frame 22, to reduce the spreading area of the monomolecular film to offset the surface pressure reduction of the monomolecular film and to maintain the same surface pressure.

As stated above, various delicate adjustments are required to obtain a monomolecular built-up film. According to conventional practices, optimum conditions for producing a built-up film have to be inconveniently selected from various tests, and whether or not the monomolecular film on the liquid surface 3 is in a condition suitable for building-up can be checked only indirectly from its surface pressure, etc., resulting in a lack of accuracy. However, when the present invention is used in place of the above mentioned surface pressure tester, the characteristic of the monomolecular film on the liquid surface 3 can be measured when the film is formed and each film can be built up under optimum conditions.

Figure 9:
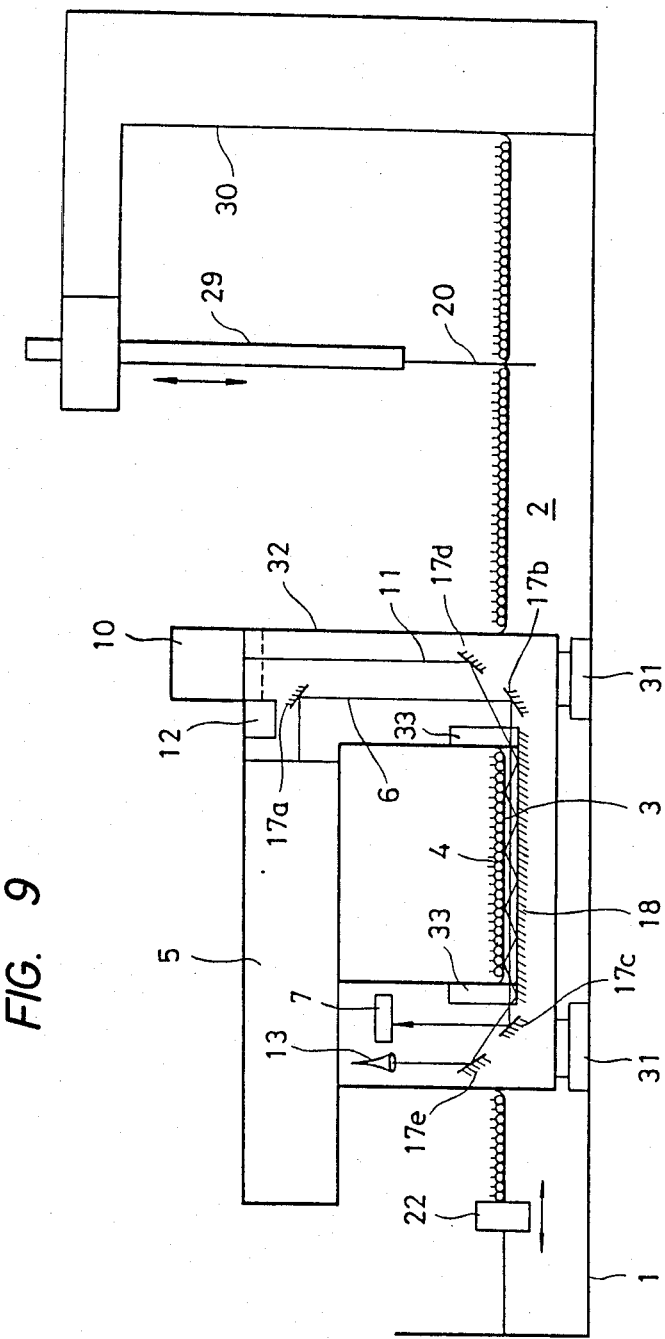
FIG. 9 is a drawing showing a preferable embodiment of the present invention for the formation of a monomolecular built-up film.
Figure 10A:
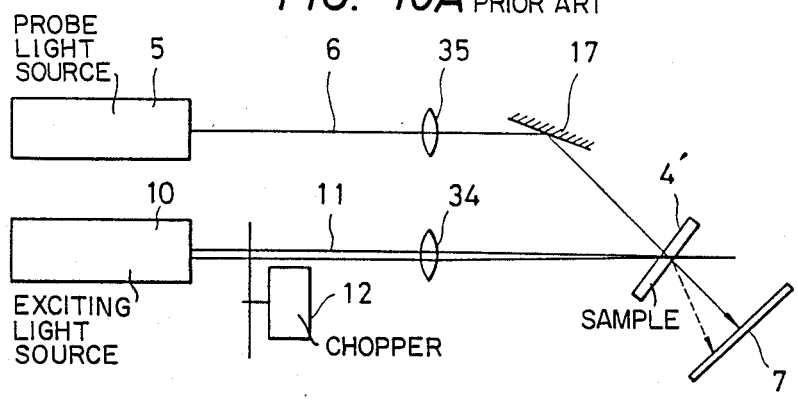
FIGS. 10A and 10B each are a drawing showing a prior art device.
Figure 10B:
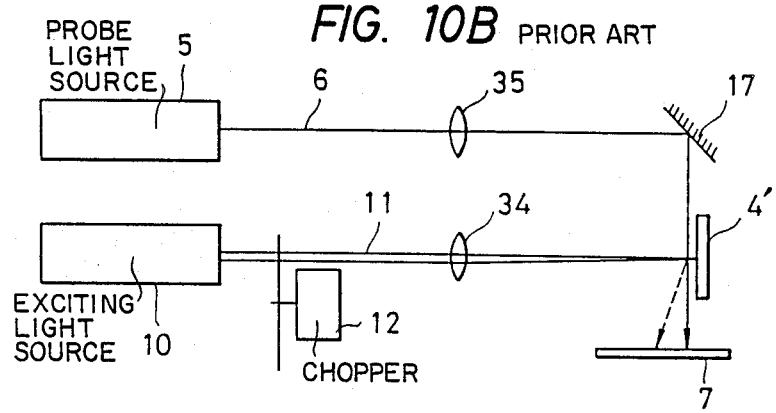

A preferable embodiment of the present invention for the formation of a monomolecular built-up film will be described in connection with FIG. 9.

At one side of a liquid container 1 containing a liquid 2 is provided a standing support 30. To this support 30 is provided a substrate holder 29 holding a substrate 20 so that the substrate 20 can move vertically to and against a liquid surface 3. At the bottom of the liquid container 1 is provided an elevating device 31, on which is provided a measurement unit 32.

The measurement unit 32 has a hollow square form like a donut and has a mirror surface at its inner bottom portion. The position of the measurement unit 32 is adjusted by the elevating device 31 so that this mirror surface is located directly under and parallel to the liquid surface 3. Inside the measurement unit 32 are provided a probe light source 5, a detector 7, light path regulating means 17a to 17c for guiding a probe light 6 supplied from the probe light source 5 to the detector 7 through a liquid portion between the liquid surface 3 and the mirror surface 18, an exciting light source 10, a chopper 12 for converting an exciting light 11 supplied from the exciting light source 10 to an intermittent exciting light, an absorber 13, and light path regulating means 17d to 17e for allowing the exciting light 11 to cause multiple reflections in a liquid portion between the liquid surface 3 and the mirror surface 18 and then guiding the exciting light 11 to the absorber 13. The lowermost portions of the inner sides of the measurement unit 32 each take the form of a window 33 through which the probe light 6 and the exciting light 11 can pass when the measurement unit 32 is not connected to the liquid 2 reference numeral. 22 refers to a film formation frame for adjusting the surface pressure of a thin film 4, which is a monomolecular film.

As described with respect to FIG. 5, the above described embodiment can measure the light absorption characteristic of the thin film 4 with high sensitivity. Another feature of this embodiment, is that the light absorption characteristic of the thin film 4 can be measured simultaneously with its formation in the form of a monomolecular film and the characteristic of the monomolecular film can be easily analyzed therefrom and as a result a monomolecular built-up film can be formed on the substrate 22 with high precision. Further, since the above discussed embodiment is designed as a unified structure, external influences on the measurements can be made small. Furthermore, attaching and detaching of the measurement unit 32 to and from the liquid container 1 is easy.

According to the present invention, in measurement of the light absorption characteristic of a thin film spread on a liquid surface, the influence of a reflected light and a transmitted light, as well as the adverse effect caused by passing an exciting light through the air can be avoided, whereby measurements of high sensitivity and high precision can be made.

What we claimed is:

1. An apparatus for measuring a light absorption characteristic of a thin film, comprising:
    a container containing a liquid having a surface for receiving a thin film thereon;
    an exciting light source for supplying exciting light to be proejcted from below the liquid surface onto a measurement site of the thin film spread on the liquid surface at an incident angle such that the exciting light reflects totally at the liquid surface;
    a mirror surface arranged under the liquid surface in the vicinity of the measurement site and at the position that the exciting light can be reflected plural times;
    a light intermitting means for converting the exciting light into an intermittent exciting light before the exciting light reaches the measurement site of the thin film;
    a probe light source for supplying probe light passing through the measurement site or its vicinity; and
    a detector for detecting the amount of deflection of the probe light having passed through the measurement site or its vicinity.

2. An apparatus according to claim 1, further comprising a medium provided over the liquid surface in the vicinity of the measurement site, wherein the refractive index of said medium changes substantially in response to heating of said medium.

3. An apparatus according to claim 2, wherein the medium is a material selected from the group consisting of:
    lithium niobate crystal, titanium oxide crystal, silicon dioxide crystal, glass, and plastic.

4. An apparatus for measuring the light absorption characteristic of a thin film, which comprises:
    a container containing a liquid having a surface, part of which is covered with a thin film, and of which is left uncovered;
    an exciting light source for supplying exciting light;
    a light path splitting means for splitting the exciting light into: (a) an exciting light portion to be projected from below the liquid surface onto a measurement site of the thin film spread on the liquid surface at an incident angle such that the exciting light portion (a) reflects totally at the liquid surface; and (b) an exciting light portion to be applied from below the liquid surface to a reference site of the uncovered part of the liquid surface at an incident angle such that the exciting light portion (b) reflects totally at the liquid surface;
    mirror surfaces arranged under the liquid surface in the vicinity of the measurement site and in the vicinity of the reference site and at the position that the exciting light can be reflected plural times, respectively;
    a light intermitting means for converting the exciting light into intermittent exciting light before the exciting light reaches the measurement site and the reference site;
    a probe light source for supplying probe light;
    a light path splitting means for splitting the probe light supplied into: (a) a probe light portion passing through the measurement site or its vicinity; and (b) a probe light portion passing through the reference site or its vicinity; and
    a detector for detecting the amount of deflection of the probe light portion (a) having passed through the measurement site or its vicinity and the probe light portion (b) having passed through the reference site or its vicinity.

5. An apparatus according to claim 4, further comprising a medium provided over the liquid surface in the vicinity of the measurement site and in the vicinity of the reference site, wherein the refractive index of said medium undergoes a substantial change in response to the heating of said medium.

6. An apparatus according to claim 5, wherein the medium is a material selected from a group consisting of: lithium niobate crystal, titanium oxide crystal, silicon dioxide crystal, glass, and plastic.

7. An apparatus according to claim 4, wherein the light path splitting means is a beam splitter or a half mirror.

8. A method for measuring a light absorption characteristic of a thin film, wherein said method comprises the steps of:
    intermittently projecting exciting light onto a measurement site of a thin film spread on a liquid surface;
    simultaneously projecting a probe light to the measurement site or its vicinity;
    measuring the amount of deflection of the probe light and determining therefrom the light absorption characteristic of the thin film, wherein the exciting light is projected to the measurement site of the thin film from the liquid side of the liquid surface at an incident angle such that the projected exciting light reflects totally at the liquid surface; and reflecting the exciting light plural times between the thin film and the mirror arranged under the liquid surface in the vicinity of the measurement site.

9. An apparatus comprising:

means for forming a monomolecular built-up film; and means for measuring the light absorption characteristic of a monomolecular film, the measuring apparatus comprising:

an exciting light source for supplying an exciting light to be projected to a measurement site of a monomolecular film spread on a liquid surface from below the liquid surface at an incident angle such that the exciting light reflects totally on the liquid surface;

a mirror surface arranged under the liquid in the vicinity of the measurement site and at the position that the exciting light can be reflected plural times;

a light intermitting means for converting the exciting light into an intermittent exciting light before the exciting light reaches the measurement site;

a probe light source for supplying a probe light passing through the measurement site or its vicinity; and a detector for detecting an amount of deflection of the probe light having passed through the measurement site or its vicinity.

10. An apparatus according to claim 9, wherein the measuring means further comprises a medium provided over the liquid surface in the vicinity of the measurement site, wherein the refractive index of said medium undergoes a substantial change in response to heating said medium.

11. An apparatus according to claim 10, wherein the medium is a material selected from the group consisting of: lithium niobate crystal, titanium oxide crystal, silicon dioxide crystal, glass, and plastic.

* * * * *